(12) United States Patent
Yeager

(10) Patent No.: US 6,872,077 B2
(45) Date of Patent: Mar. 29, 2005

(54) SYSTEM AND METHOD FOR GENERATING PERSONALIZED MEAL PLANS

(76) Inventor: John J. Yeager, 11141 Cashmere St., Los Angeles, CA (US) 90049

( * ) Notice: Subject to any disclaimer, the term of this patent is extended or adjusted under 35 U.S.C. 154(b) by 9 days.

(21) Appl. No.: 09/948,317

(22) Filed: Sep. 6, 2001

(65) Prior Publication Data

US 2003/0091964 A1 May 15, 2003

(51) Int. Cl.$^7$ .............................................. G09B 11/00
(52) U.S. Cl. ..................................................... 434/127
(58) Field of Search ................................ 434/127, 322, 434/236–8; 705/2, 14, 26; 600/300

(56) References Cited

U.S. PATENT DOCUMENTS

| | | | |
|---|---|---|---|
| 4,650,218 A | | 3/1987 | Hawke ........................ 283/67 |
| 4,951,197 A | * | 8/1990 | Mellinger ................... 600/300 |
| 5,454,721 A | * | 10/1995 | Kuch .......................... 434/127 |
| 5,639,471 A | | 6/1997 | Chait et al. .................. 424/439 |
| 5,673,691 A | * | 10/1997 | Abrams et al. .............. 600/300 |
| 5,969,316 A | | 10/1999 | Greer et al. ................. 235/375 |
| 6,024,281 A | | 2/2000 | Shepley ....................... 235/375 |
| 6,040,531 A | | 3/2000 | Miller-Kovach et al. ........................ 177/25.16 |
| 6,185,541 B1 | * | 2/2001 | Scroggie et al. .............. 705/14 |
| 6,618,062 B1 | * | 9/2003 | Brown et al. ................ 345/810 |
| 2001/0025279 A1 | * | 9/2001 | Krulak et al. .................. 707/3 |
| 2001/0051901 A1 | * | 12/2001 | Hager et al. ................... 705/26 |
| 2002/0046060 A1 | * | 4/2002 | Hoskyns et al. ................ 705/2 |
| 2002/0120496 A1 | * | 8/2002 | Scroggie et al. .............. 705/14 |

OTHER PUBLICATIONS

Provisional application 60/222986.*

* cited by examiner

Primary Examiner—Xuan M. Thai
Assistant Examiner—Kathleen M. Christman
(74) Attorney, Agent, or Firm—Sheppard, Mullin, Richter & Hampton, L.L.P.

(57) ABSTRACT

A system for personalized meal planning is provided which includes a client device and a meal planning center configured to communicate with the client device and to receive a customer's information, including a weight designator, a gender designator, a goal designator, and an activity level designator. The meal planning center includes a storage device and a processing unit. The storage device is configured to store recipe template files having an ingredient designator and a plurality of recipe rule factors, which include a nutrient contribution value, a minimum ingredient value, and a maximum ingredient value. A plurality of recipe rule factors are each assigned to each ingredient designator. The processing unit is configured to determine a nutritional allowance based upon the customer information and to create a recipe that satisfies the nutritional allowance by using the recipe rule factors assigned to the ingredient. The meal planning center is further configured to transmit the recipe to the client device.

9 Claims, 17 Drawing Sheets

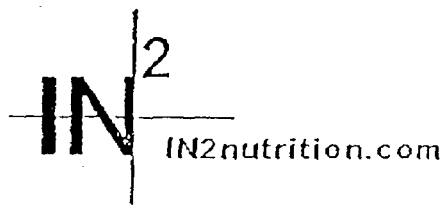

IN2nutrition.com

Email:
Password:
(?) Member Login

FUELED BY IN2

Personalized Nutrition Plans

IN2 analyzes your exact nutrition needs and instantaneously provides you with over 250 personalized recipes and meal options that guarantees to improve your health, fitness and physical condition. Your weekly meal plan is both nutritionally and metabolically balanced which stabilizes blood sugar levels, increases metabolism, strengthens muscle tissue and quickly burns unnecessary body fat.

This comprehensive system incorporates high quality foods into a personalized plan to meet your exact training, medical and lifestyle needs. From professional athletes and fitness enthusiasts to individuals with medical concerns, IN2 guarantees you immediate, safe and lifelong results.

Subscribe Today!   Tell Me More   Success Stories

© 2001. All Rights Reserved.

Step 2: Registration

──── Reference Code (if any) ────

Reference Code

──── General ────

82 ──Email Address
80 ──Password

84 ──First name
   Middle initial
   Last name

86 ──Address
   Suite
   City
   State
   Zip
   Phone
   Fax

──── Vital stats ────

64 ──Gender     ⦿ Female   ○ Male

66 ──Birthdate (e.g 12/31/55)
   Height    5' 5"
68 ──Weight    lbs
   Body Frame    small   [ Help ]
70 ──Body Fat    % [ Help ]

72 ──Goals (please select one)

○ Maximum Fat Loss - Ideal for individuals with obesity diabetes who would like to increase energy and need to more than 15 pounds of body fat ⦿ Moderate Fat Loss - Ideal for individuals who would like increase energy and need to lose less than 15 pounds o fat. This is also a great selection for diabetics.

○ Maintenance - Ideal for individuals who are satisfied with their current weight who want to increase energy and tone their body.

○ Build Muscle - Ideal for individuals who are currently exercising on a regular basis and would like to increase white building muscle mass.

○ Athletic Performance - Ideal for competitive athletes want to increase energy and maximize performance.

FIG. 6

Meal Plan

74 — Meal Program

⦿ Basics
Ideal for those constantly on-the-go who don't have tim cook. This plan uses approximately 50 items found at a grocery store and requires a microwave for some meals Average meal preparation time is 5 minutes.

○ Basics Plus
Great for those with a busy lifestyle who don't mind usit stove and microwave to prepare meals. This plan uses approximately 70 items found at a local grocery store. Average meal preparation time is 10 minutes.

○ Elite
Perfect for those who do not mind shopping and cookinç Preparation time is 15 mins and uses 135 items from th grocery store.

○ Comprehensive
Ideal for the individual that loves to cook. This program the widest variety and average preparation time is 20 minutes.

76 — Food Preferences

|  | Include | Remove |
|---|---|---|
| Beef | ⦿ | ○ |
| Chicken | ⦿ | ○ |
| Dairy | ⦿ | ○ |
| Lamb | ⦿ | ○ |
| Pork | ⦿ | ○ |
| Protein Powder | ⦿ | ○ |
| Seafood | ⦿ | ○ |
| Tuna | ⦿ | ○ |
| Turkey | ⦿ | ○ |

73 — Time you typically eat your first meal [08:00 AM ▼]

Exercise

78 — Current Activity Level

⦿ None
currently do not exercise or engage in regular physical activity.

○ Fat Loss Focus
walk or primarily participate in cardiovascular exercise for 20-30 minutes at least 3-4 times per week. heart rate is slightly increased.

○ Good Health
exercise somewhat intensely for 30-40 minutes at least 4 times per week. exercise primarily consists of cardio but includes some resistance training. heart rate is increased 70% of maximum at least half of the time.

○ Strength Training
exercise intensely for 45 minutes at least 5-6 times per exercise primarily consists of resistance training with so

FIG. 6 (Cont.)

cardio. heart rate is increased to 70% of maximum at least three quarters of the time. Do not select this activity factor if you are trying to lose fat as your primary goal.

○ Muscle Building / Athletic Performance
exercise intensely for at least 1 hour 6-7 times per week training consist of heavy weight lifting and or performar based endurance training.

○ Competitive Athlete
exercise very intensely for at least 2 hours 6-7 times pe week. training consists of heavy weight lifting and or performance based endurance training.

Generate exercise plan (optional)
Days per week 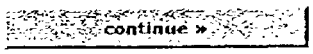
Equipment
  ○ Home
  ○ Gym

 continue »

☐ Secure
▇ Area

Copyright © 2001. All Rights Reserved.

FIG. 6 (cont.)

| ID | Name | Unit | Msrmnt. | C | P | F | SF | Fbr | Sod | Sug | Status |
|---|---|---|---|---|---|---|---|---|---|---|---|
| 95 | lamb, lean | 1 | | 0.0 | 7.0 | 3.0 | 0 | 0 | 20 | 0 | Yes |
| 458 | Lamb, trimmed to 1/4 fat | 1 | oz | 0.0 | 6.0 | 1.0 | 1 | 0 | 21 | 0 | Yes |
| 761 | Land O' Lakes Whipped Classic Blend | 1 | oz | 0.0 | 0.0 | 7.0 | | 0 | 75 | 0 | No |
| 1687 | Large Fries | 1 | | 31.0 | 28.0 | 9.0 | | 7 | 1000 | | No |
| 2103 | Large Fries | 1 | | 46.0 | 5.0 | 24.0 | 4 | | 830 | | No |
| 2004 | Lasagna Bake | 1 | | 43.0 | 15.0 | 6.0 | 2 | 5 | 600 | 6 | Yes |
| 2017 | Lasagna Bolognese - Smart Ones | 1 | | 43.0 | 13.0 | 2.5 | 1 | 4 | 550 | 5 | Yes |
| 2037 | Lasagna Florentine - Smart Ones | 1 | | 36.0 | 15.0 | 8.0 | 4.5 | 5 | 650 | 3 | Yes |
| 1904 | Latte, lowfat milk, grande | 1 | | 22.0 | 14.0 | 8.0 | 5 | 0 | 220 | na | Yes |
| 1905 | Latte, lowfat milk, short | 1 | | 11.0 | 7.0 | 4.0 | 2.5 | 0 | 110 | na | Yes |
| 1906 | Latte, lowfat milk, tall | 1 | | 17.0 | 11.0 | 6.0 | 4 | 0 | 170 | na | Yes |
| 1907 | Latte, lowfat milk, venti | 1 | | 28.0 | 19.0 | 10.0 | 6 | 0 | 280 | na | Yes |
| 1908 | Latte, nonfat milk, grande | 1 | | 23.0 | 15.0 | 1.0 | 0.5 | 0 | 220 | na | Yes |
| 1909 | Latte, nonfat milk, short | 1 | | 11.0 | 7.0 | 0.0 | 0 | 0 | 110 | na | Yes |
| 1910 | Latte, nonfat milk, tall | 1 | | 17.0 | 12.0 | 0.5 | 0 | 0 | 170 | na | Yes |
| 1911 | Latte, nonfat milk, venti | 1 | | 29.0 | 19.0 | 1.0 | 0.5 | 0 | 280 | na | Yes |
| 1912 | Latte, soy milk, grande | 1 | | 10.0 | 12.0 | 8.0 | 1 | 0 | 50 | na | Yes |
| 1913 | Latte, soy milk, short | 1 | | 5.0 | 6.0 | 4.0 | 0 | 0 | 25 | na | Yes |
| 1914 | Latte, soy milk, tall | 1 | | 7.0 | 9.0 | 6.0 | 0.5 | 0 | 40 | na | Yes |
| 1915 | Latte, soy milk, venti | 1 | | 12.0 | 15.0 | 10.0 | 1 | 0 | 65 | na | Yes |
| 1916 | Latte, whole milk, grande | 1 | | 22.0 | 14.0 | 14.0 | 9 | 0 | 210 | na | Yes |
| 1917 | Latte, whole milk, short | 1 | | 11.0 | 7.0 | 7.0 | 4.5 | 0 | 105 | na | Yes |
| 1918 | Latte, whole milk, tall | 1 | | 17.0 | 11.0 | 11.0 | 7 | 0 | 160 | na | Yes |
| 1919 | Latte, whole milk, venti | 1 | | 28.0 | 18.0 | 18.0 | 12 | 0 | 270 | na | Yes |

FIG. 8A

| tomato | | |
|---|---|---|
| Name | tomato | Options |
| Single Display Name | tomato | |
| Multiple Display Name | tomatoes | |
| Unit | .5 | |
| Measurement | medium | |
| Source | Carbohydrate | Notes: Good source of potassium, dietary fiber and vitamins A and C. Glycemic Index: excellent |
| Brand | | |
| Meal Program Scope | 1 | |
| Grams | 62 | Preparation |
| Carbohydrates | 5.0 | |
| Protein | 0.0 | |
| Fat | 0.0 | |
| Saturated fat | 0 | |
| Fiber | 1 | |
| Sodium | 11 | |
| Sugar | 0 | |
| Calories | 20 | |
| Add To Shopping List | ⊙ Yes ○ No | |
| Fast Food | ○ Yes ⊙ No | |
| Shopping Category | Produce | |
| II/2 Approved | ⊙ Yes ○ No | |
| Active | ⊙ Yes ○ No | | update | reset

Ahi Tuna in Lemon-Caper Sauce

Recipe Definition | Active Ingredients

| Ingredient | Unit | Scope | Base C | Base P | Base F | Function | Type | Prty | Factors Dft | Factors Max | Factors Min | Subtotal C | Subtotal P | Subtotal F | | |
|---|---|---|---|---|---|---|---|---|---|---|---|---|---|---|---|---|
| capers | 1 tsp | 4 | 0.0 | 0.0 | 0.0 | none | Ingredients | | 1.0 | 1.0 | 1.0 | 0 | 0 | 0 | edit | delete |
| lemon juice | 1 tsp | 1 | 0.0 | 0.0 | 0.0 | none | Ingredients | | 3.0 | 3.0 | 3.0 | 0 | 0 | 0 | edit | delete |
| mushrooms | .5 cup | 1 | 2.0 | 10.0 | 0.0 | carbohydrate factor | Ingredients | 1 | 1.0 | 4.0 | 1.0 | 2 | 0 | 0 | edit | delete |
| oil, high oleic safflower | .5 tsp | 1 | 0.0 | 0.0 | 2.5 | fat factor | Ingredients | 1 | 3.0 | 10.0 | 3.0 | 0 | 0 | 7.5 | edit | delete |
| onion | .25 cup | 1 | 2.0 | 0.0 | 0.0 | none | Ingredients | | 1.0 | 1.0 | 1.0 | 2 | 0 | 0 | edit | delete |
| pasta | .25 cup | 2 | 10.0 | 0.0 | 0.0 | none | Ingredients | | 3.0 | 3.0 | 3.0 | 30 | 0 | 0 | edit | delete |
| tomato | .5 medium | 1 | 5.0 | 0.0 | 0.0 | carbohydrate factor | Ingredients | 2 | 0.0 | 4.0 | 0.0 | 0 | 0 | 0 | edit | delete |
| tuna, ahi | 1 oz | 3 | 0.0 | 6.0 | 0.0 | protein factor | Ingredients | 1 | 3.0 | 6.0 | 3.0 | 0 | 18 | 0 | edit | delete |
| | | | | | | | | | | | | 34 | 18 | 7.5 | add | |

FIG. 10

Demo's meal plan

Thursday, August 30

Edit | Print

|  |  |  | carbs | protein | fat |
|---|---|---|---|---|---|
| 08:00 AM | Chicken Breakfast Tortilla | | 61 | 34 | 8 |
| 11:00 AM | Turkey and Crackers | | 59 | 35 | 7 |
| 02:00 PM | Chicken Salad | | 57 | 38 | 8 |
| 05:00 PM | Italian Custard with Pears | | 62 | 35 | 9 |
| 08:00 PM | Beef and Bean Tortilla | | 57 | 36 | 9 |
| | Calories: 2,250 | | 296 | 178 | 41 |

Friday, August 31

Edit | Print

|  |  |  | carbs | protein | fat |
|---|---|---|---|---|---|
| 08:00 AM | Oatmeal with Peaches and Egg Whites | | 59 | 36 | 8 |
| 11:00 AM | Strawberry Nut Yogurt | | 61 | 35 | 9 |
| 02:00 PM | Ham and Cheese Sandwich | | 55 | 33 | 11 |
| 05:00 PM | Chocolate Banana Shake | | 58 | 36 | 0 |
| 08:00 PM | Eggplant Parmesan | | 60 | 36 | 7 |
| | Calories: 2,252 | | 293 | 176 | 43 |

Saturday, September 01

Edit | Print

|  |  |  | carbs | protein | fat |
|---|---|---|---|---|---|
| 08:00 AM | Peanut Butter Waffles | | 59 | 34 | 8 |
| 11:00 AM | Chocolate Peanut Butter Nutrition Bar | | 56 | 36 | 7 |
| 02:00 PM | Chopped Salad | | 61 | 35 | 9 |
| 05:00 PM | Cottage Cheese and Apricots | | 58 | 34 | 9 |
| 08:00 PM | Tuna Stir-Fry | | 60 | 38 | 8 |
| | Calories: 2,238 | | 294 | 177 | 41 |

- Print all meals — 128
- Shopping list
- Store Locator
- Cookbook
- Need Help?

| Aug | | | 2001 | | | |
|---|---|---|---|---|---|---|
| Sun | Mon | Tue | Wed | Thu | Fri | Sat |
| | | | 1 | 2 | 3 | 4 |
| 5 | 6 | 7 | 8 | 9 | 10 | 11 |
| 12 | 13 | 14 | 15 | 16 | 17 | 18 |
| 19 | 20 | 21 | 22 | 23 | 24 | 25 |
| 26 | 27 | 28 | 29 | 30 | 31 | |

Today is Thursday, Aug 30 show meals for [3 days]

FIG. 11

Print Shopping List

Ingredient      Brand      Source

Produce
- 1 medium orange      Carbohydrate
- 9 medium tomatoes      Carbohydrate
- 5 ½ cups iceberg lettuce
- ¾ cup onion      Carbohydrate

Meats and Poultry
- 2 oz lean ground beef      Protein / Fat

Deli
- 5 slices deli-style ham      Protein
- 7 slices deli-style turkey breast      Healthy Choice      Protein

Eggs and Dairy
- 2 tsp low-fat cream cheese      Kraft      Carb / Protein / Fat
- 30 egg whites      All Whites      Protein
- ½ cup low-fat milk      Alta Dena      Carb / Protein
- ½ cup low-fat cottage cheese      Knudsen's      Carb / Protein / Fat
- 14 tbl low-fat yogurt, plain      Dannon      Carb / Protein
- 4 oz non-fat cheddar cheese      Lifetime      Protein
- ¾ cup skim ricotta cheese      Knudsen's      Carb / Protein / Fat
- 5 oz non-fat mozarella cheese      Lifetime      Protein
- 2 tsp parmesan cheese      Kraft      Protein / Fat

Bread and Baked Goods
- 3 slices Ezekiel flourless bread (substitutes: rye or pumpernickel)      Ezekiel      Carb / Protein
- 3 corn tortillas      Carbohydrate

FIG. 12

Demo's profile

GENERAL
- Your profile
- Password
- Update
- Assessment
- Nutrition Formula

SETTINGS
- Cookbook
- Inactive Recipes
- Update alert
- Payment update profile

Demo, your profile was last update on August 30, 2001. Your next profile update is scheduled for September 20, 2001

| Last update | | Current |
|---|---|---|
| 200 | Body Weight | ☐ |
| 10 | Body Fat [ Help ] | ☐ |

How are you feeling?
- great ⦿
- very good ○
- ok ○
- could be better ○
- does not seem to be working ○
- just need moral support ○ update

Note: We recommend you also update your Activity level, Goals, Body measurements, and Health data in your profile.

FIG. 13

SYSTEM AND METHOD FOR GENERATING PERSONALIZED MEAL PLANS

BACKGROUND OF THE INVENTION

1. Field of the Invention

The present invention relates generally to meal planning and, more particularly, to a meal planning system, and related method, for generating personalized meal plans.

2. Description of the Related Art

It is well known in the art that a proper diet is important to a person's health and well being. Traditionally, diet plans have addressed a single goal, e.g., weight loss. Towards that end, such diet plans primarily focused on limiting daily caloric intake. These diets would assign the person a daily caloric intake amount, which is derived from a standardized formula or chart based on factors such as age, gender, height and body weight. The corresponding meal plan to this dietary approach would be established by satisfying the daily caloric intake amount.

As diet plans advanced, the factors and formulas used to create corresponding meal plans have become increasingly complex. Some diet plans have focused on a person's fat and fiber intake. Other diet plans are based on fixed ratios of macronutrients such as fats, proteins, and carbohydrates, while varying daily caloric intake based on some standardized factors or formulas. Still other diet plans vary the ratios of macronutrients based only on complex formulas accounting for factors such as the customer's metabolic rate, exercise regime, and health objectives. The formulas associated with these types of diets provide precise, personalized values for daily intake of macronutrients. Such diet plans, if followed, have been generally effective in achieving the person's health objectives. However, determining the proper daily amount of macronutrients can be complicated and time consuming. It is not practical to use generalized recipes under such diet plans, since the appropriate ratios of macronutrients and total calories per day vary with each individual. Furthermore, generating personalized recipes to fulfill these daily requirements requires considerable time and effort.

It should, therefore, be appreciated that there is a need for a cost-effective system and method that provides personalized meal plans optimized to achieve a selectable health objective, which requires minimal research, effort, time, computation and record keeping. The present invention fulfills this need as well as others.

SUMMARY OF THE INVENTION

A system for personalized meal planning is provided which includes a client device and a meal planning center configured to communicate with the client device, and to receive a customer's information including a weight designator, a gender designator, a goal designator, and an activity level designator. The meal planning center includes a storage device and a processing unit. The storage device is configured to store recipe template files having an ingredient designator and a plurality of recipe rule factors, which include a nutrient contribution value, a minimum ingredient value, and a maximum ingredient value. A plurality of recipe rule factors are each assigned to each ingredient designator. The processing unit is configured to determine a nutritional allowance based upon the customer information and to create a recipe that satisfies the nutritional allowance by using the recipe rule factors assigned to the ingredient. The meal planning center is further configured to deliver the recipe to the client.

A method for personalized meal planning is also provided which includes receiving at the meal planning center a customer's information including a weight designator, a gender designator, a goal designator, and an activity level designator. The meal planning center calculates a nutritional allowance based on the customer's information, and selects a recipe template file having an ingredient designator and a plurality of recipe rule factors from a recipe template database. The selected recipe template file is used by the meal planning center to create a recipe that satisfies the nutrition allowance, and delivers the recipe to the client.

Advantages of the present invention include providing a personalized meal plan adapted to achieve selectable health objectives. Furthermore, the present invention reduces the knowledge and effort required to develop and maintain a personalized meal plan, which in turn increases an individual's chances of achieving their health objectives.

Other features and advantages of the invention should become apparent from the following description of the preferred embodiment, taken in conjunction with the accompanying drawings, which illustrate, by way of example, the principles of the invention.

BRIEF DESCRIPTION OF THE DRAWINGS

Embodiments of the present invention will now be described, by way of example only, with reference to the following drawings in which:

FIG. 5 is a sample home page, which is used to begin the method of meal planning depicted in FIG. 4;

FIG. 6 is a sample customer input page, which is used with the method of meal planning depicted in FIG. 4;

FIGS. 8A and 8B are sample nutritional pages, which are used to add a recipe template to the recipe template database;

FIG. 9 is a sample meal preparation page, which is used with the method of meal planning depicted in FIG. 4;

FIG. 10 is a sample ingredients input page, which is used with the method of meal planning depicted in FIG. 4;

FIG. 11 is a sample meal plan page, which is displays the meals generated with the method of meal planning depicted in FIG. 4;

FIG. 12 is a sample shopping list depicting the ingredients used to prepare the meals of FIG. 11

FIG. 13 is a sample customer update page, which is used with the method of meal planning depicted in FIG. 4.

DESCRIPTION OF THE PREFERRED EMBODIMENT

In this section, the present invention is described in detail with regard to the figures briefly described above. As such, the following terms are used throughout the description. For purposes of construction, such terms shall have the following meanings:

The terms "client," "customer," and "user," unless otherwise specified, are intended to refer to any person, group of people, business, or other entity who uses meal planning services.

The term "recipe," unless otherwise specified, is intended to refer to instructions for a meal that might include preparation instructions, an ingredient list, and/or a meal purchase recommendation from a provider of prepared meals.

The term "meal plan," unless otherwise specified, is intended to refer to a recipe(s) or meal recommendation(s) that take into consideration factors such as time of meal, type of meal, nutritional combination and food preferences.

Figure 1:
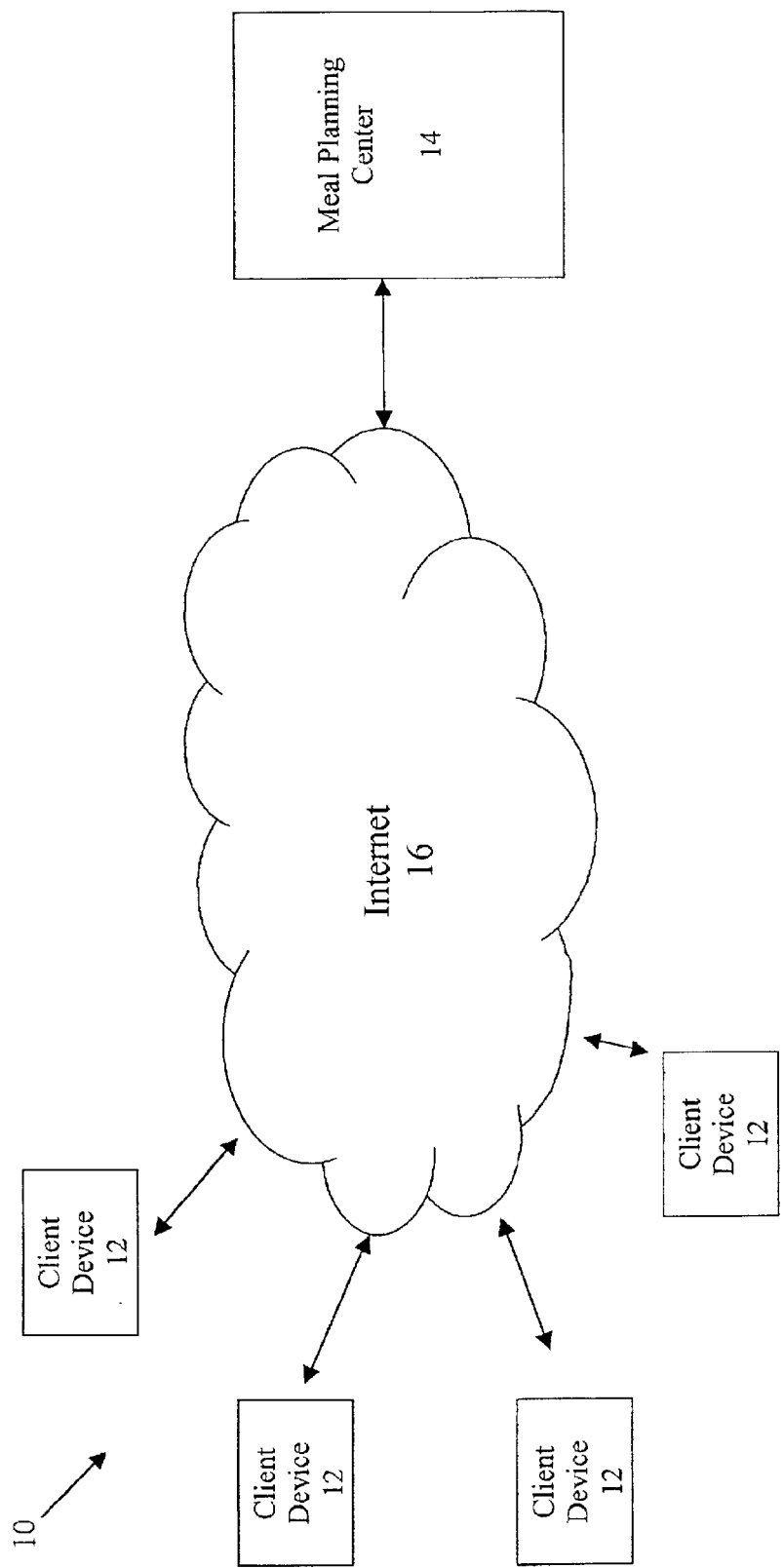
FIG. 1 is a simplified block diagram of a meal planning system.

With reference now to the illustrative drawings, and particularly to FIG. 1, there is shown a simplified block diagram of a meal planning system 10, which includes client devices 12 and a meal planning center 14 that are coupled together via the Internet 16. The connections between these components are shown using a double-sided arrow which may be a physical, fiber optic, wireless, or any other type of link. Additionally, other types of communications means and/or protocols can be used, for example, a customer can transfer information by means of a memory card and memory card reader. Furthermore, even though four client devices and one meal planning center are depicted, any number can be used. The meal planning system may be implemented using hardware, software, or a combination of the two.

Figure 2:
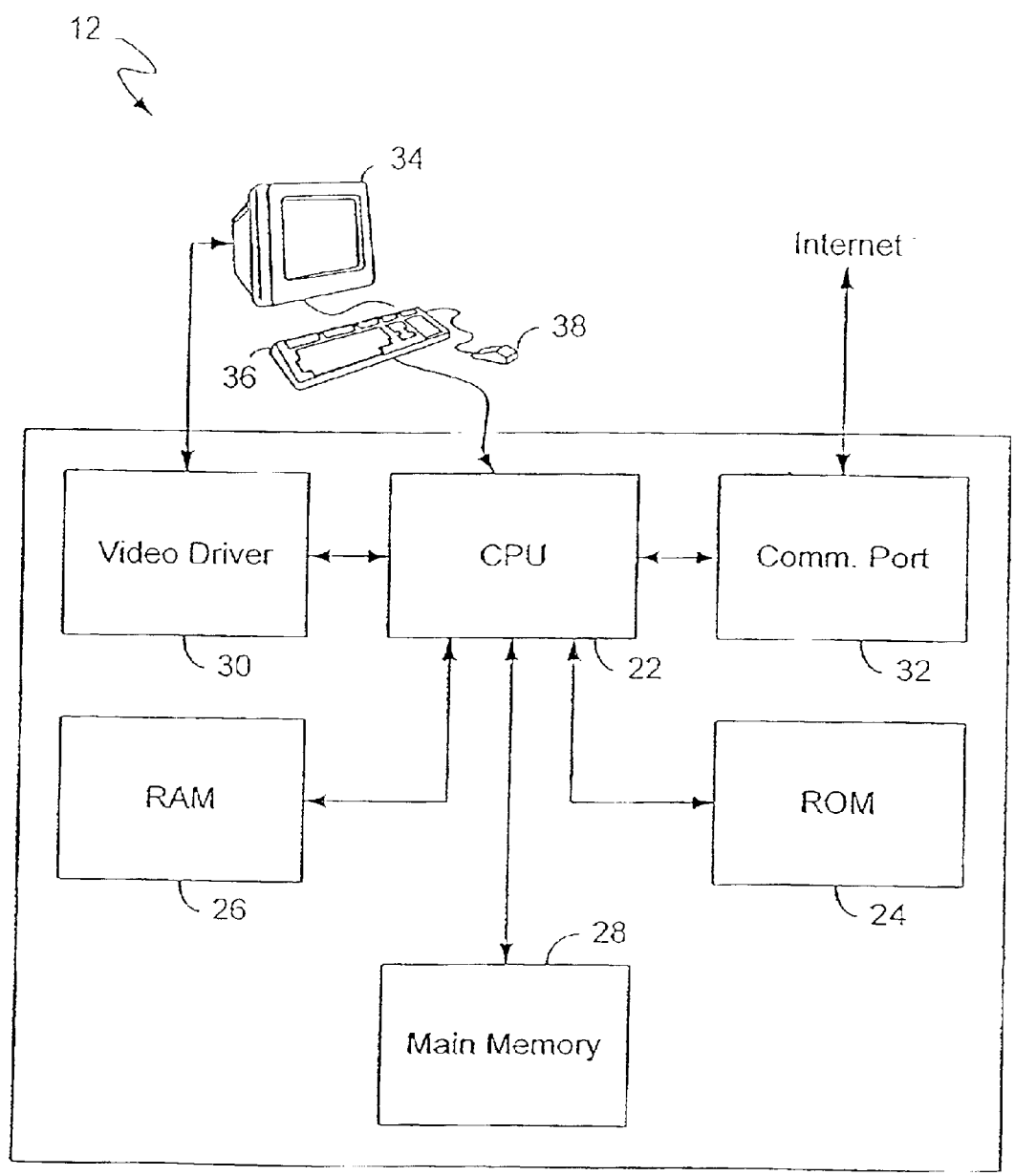
FIG. 2 is a simplified block diagram of the client device of FIG. 1.

FIG. 2 is a simplified block diagram of the client device 12 of the meal planning system 10 of FIG. 1. The client device is illustrated as a personal computer (PC), however, the client device may be any device or means sufficient to provide and/or receive information, e.g., an email, a telephone, U.S. mail, a page, or a facsimile. Additionally, the client device may be a portable web-enabled device such as a handheld device (e.g., a PalmPilot by 3Com Corporation), a cellular telephone, or a pager.

The PC includes a central processing unit (CPU) 22, a read-only memory (ROM) 24, a random-access memory (RAM) 26, a main memory 28, a video driver 30, a communication port 32, a monitor 34, a keyboard 36, and a mouse 38. The CPU executes instructions that are stored in the ROM, RAM, and main memory. The ROM is used to store some of the program instructions, the RAM is used for the temporary storage of data, and the main memory is used to store instructions and data. The video driver configures the data received from the CPU so that it can be displayed using the monitor. The keyboard and the mouse allow the customer to input information that may be sent to the meal planning center 14 via the communications port. The communication port is connected to the CPU and interfaces with a modem, cable, DSL line, wireless link, or any other technology connection that facilitates communication between the client device 12 and the meal planning center. It is understood by those of ordinary skill in the art that other methods of communicating with the meal planning center may be used instead of the modem, such as hard-wired connections, radio communications, optical communications, and the like. The use of the CPU in conjunction with the ROM, RAM, main memory, video driver, communication port, and modem is well known to those of ordinary skill in the art. A standard PC such as an IBM PC or an Apple iMac, or a handheld device, running the software of the present invention, may be used as the client device. One of ordinary skill in the art will know that the client device can vary from the components described above.

Figure 3:
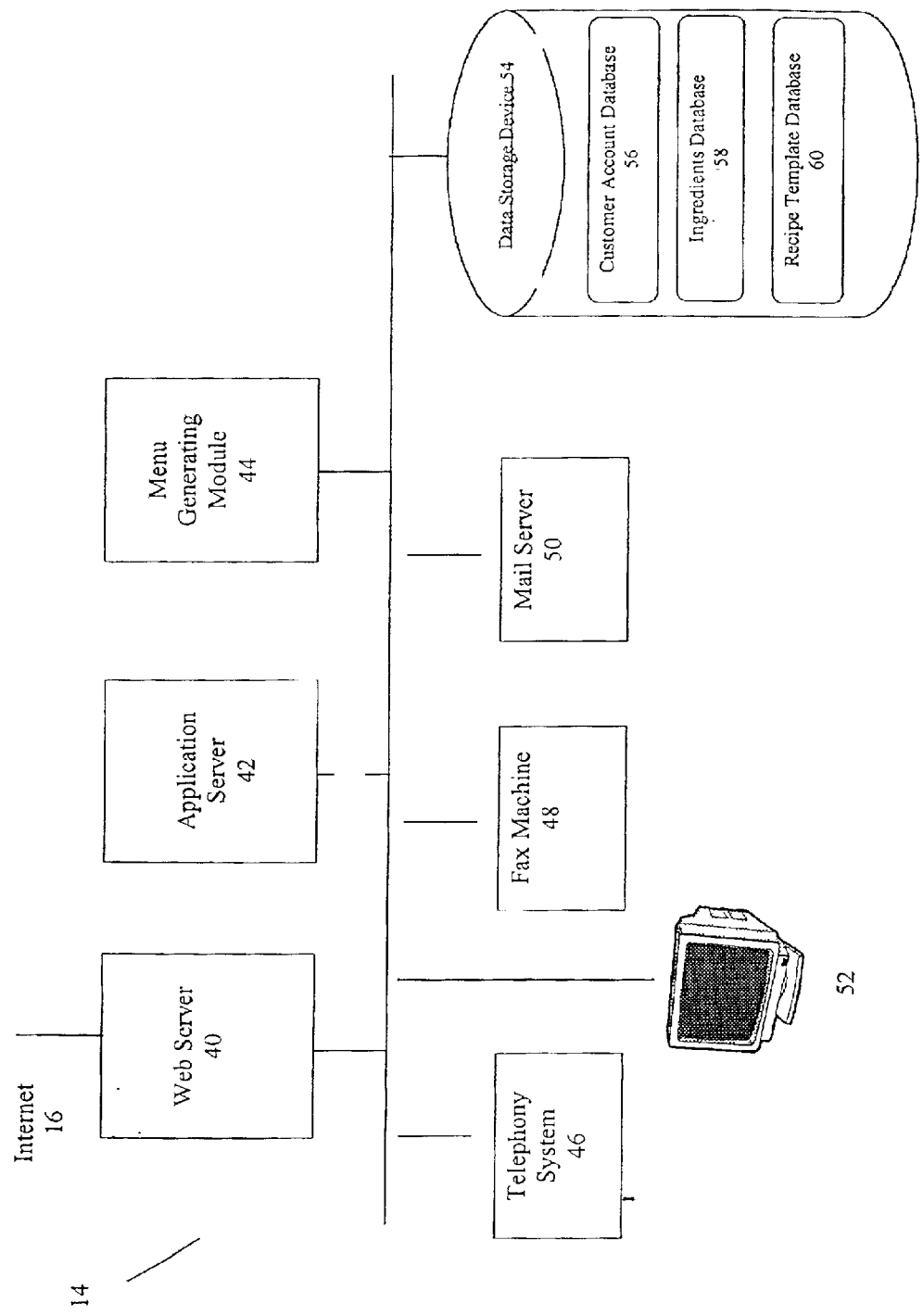
FIG. 3 is a simplified block diagram of the meal planning center of FIG. 1.

FIG. 3 is a simplified block diagram of the meal planning center 14 of the meal planning system 10 of FIG. 1. Preferably, the meal planning center includes a web server 40, an application server 42, a menu generating module 44, a telephony system 46, a fax machine 48, a mail server 50, and a terminal 52.

The web server 40 stores and runs applications for the web site of the meal planning center 14 and provides a means for connecting to the Internet 16. Multiple servers may be included in the web server to accommodate for high volume accesses to the meal planning center's web site. The application server 42 stores the applications for the web site. The application server also runs applications that direct the data and information amongst the various components, modules, and servers of the meal planning center. The menu generating module 44 uses information received from the client device 12 to produce a personalized meal plan, as discussed below. The telephony system 46 provides customers with an optional communications means with the meal planning center. The fax machine 48 can also be included as part of the meal planning center, and is used to send faxes to, and receive faxes from customers. The mail server 50 runs applications that process incoming emails from, and transmits emails to, the client device.

The meal planning center 14 further includes a data storage device 54 having a customer account database 56, an ingredients database 58, and a recipe template database 60. The customer account database stores the customer's personal information used to create the meal plan, such as gender, age, weight, percent body fat, and other pertinent information discussed below. The ingredients database stores a list of ingredients, e.g., cottage cheese, pasta, apple cider, tomatoes, egg whites, grapes, almonds, and cinnamon, and information pertaining to the ingredients, e.g., grams of carbohydrates, fat, fiber, protein, and sodium per unit of measurement. The recipe template database stores information relating to the recipes' identifying information, ingredients, nutritional factors, ingredient priorities, and recipe building factors. Alternatively, it will be appreciated that combinations of the above data into different database configurations can be done in other embodiments of this invention. Furthermore, data relating to pre-manufactured food products can be stored in one of the databases for use by the meal planning center. Additional information regarding these databases will be discussed throughout this description. The data stored in the data storage device can be read, written, and executed by the various components, servers and modules included in the meal planning center.

Figure 4:
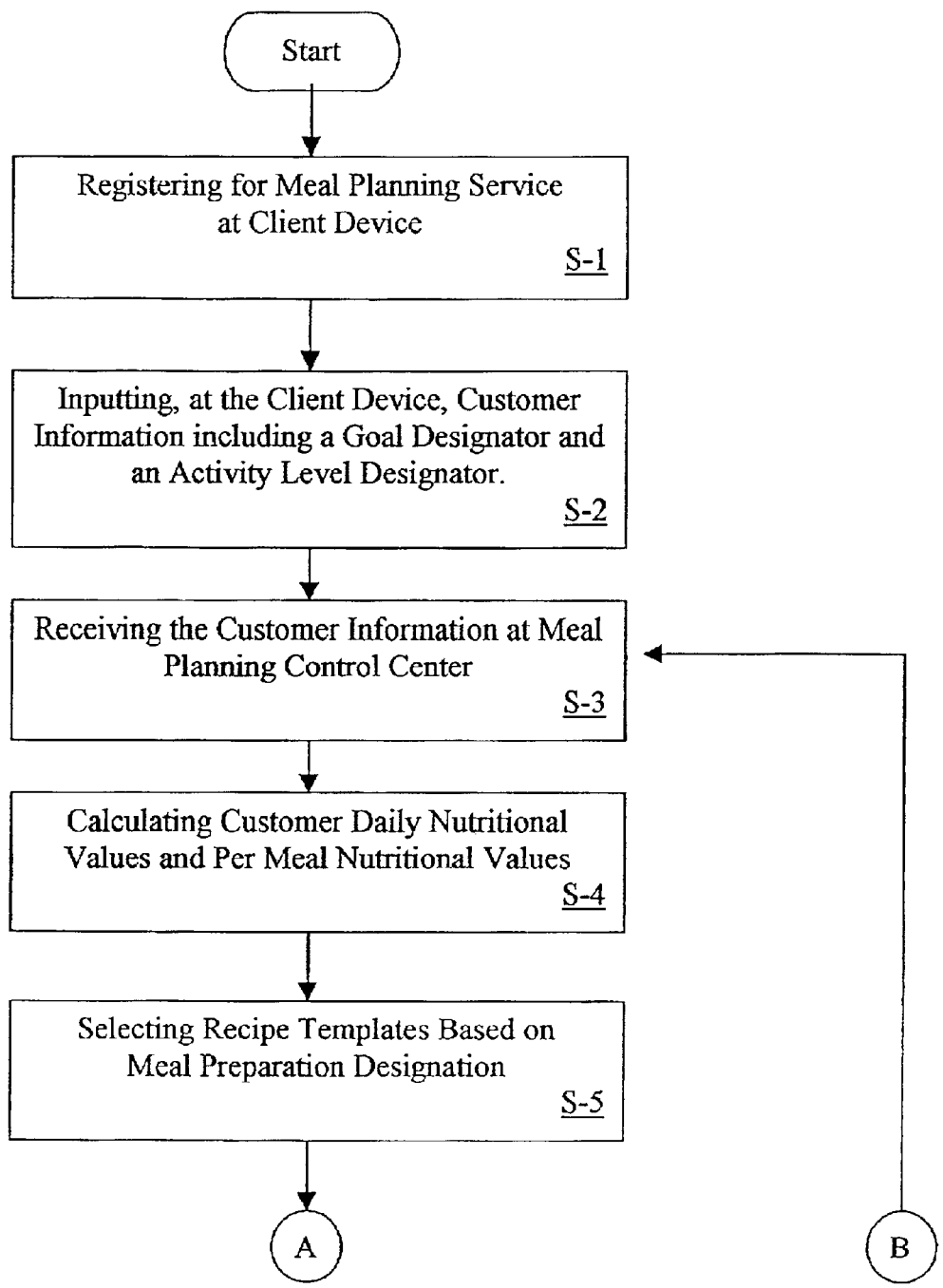
FIG. 4 is a simplified flowchart depicting a method of meal planning.
Figure 4:
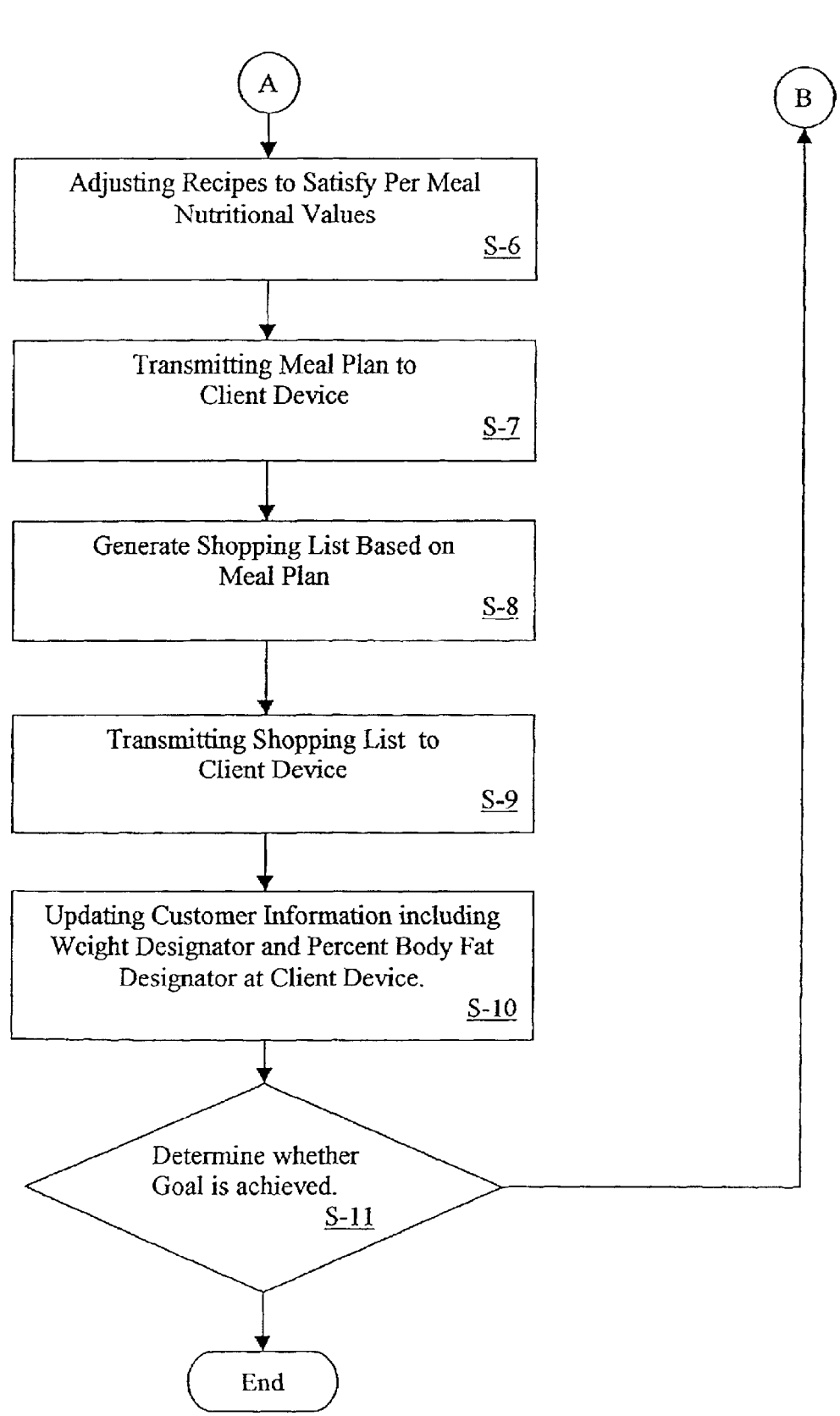

FIG. 4 is a flowchart depicting the method of creating a personalized meal plan for a selectable time period based on particular criteria provide by the customer using the meal planning system 10 of FIG. 1. The method of meal planning starts when a customer uses a client device 12 with software such as a web browser, commercially available examples of which are Netscape Navigator and Microsoft Internet Explorer, to access the Internet 16 or other link to communicate with the meal planning center 14. The customer uses the web browser and Uniform Resource Locators (URLs) to locate the meal planning center's home page. For example, using the web browser, the customer enters the URL address, e.g., www.in2nutrition.com, of the meal planning center, and the web server 40 retrieves the requested home page and transmits it over the Internet to the client device. As the web page is received by the client device, the web page is displayed on the client's monitor 34.

At step S-1, the customer registers for meal planning services, which can occur by submitting information requested on a registration page (see also FIGS. 5 and 6). The customer can access the registration page from the home page received at the client device 12. FIG. 5 is a sample home page transmitted by the web server 40 that initiates step S-1 depicted in FIG. 4. Once the home page is displayed, the customer may select, using the keyboard 36, mouse 38 or other input device, from a number of features displayed on the home page. For example, the customer may select features such as "Subscribe Today", "Tell Me More", "Success Stories", and "Member Login" by clicking the appropriate hyper-linked icon. Preferably, step S-1 is initiated by the customer selecting the "Subscribe Today" icon 62, which will direct the web server 40 to transmit a customer registration page as depicted in FIG. 6, to the client device 12.

At step S-2 of FIG. 4, the customer registration page (FIG. 6) prompts the customer to input information, namely, designators for gender 64, age 66 (i.e., the customer's birthday), weight 68, percent body fat 70, goal 72, first meal time 73, meal program 74, food preference 76, activity level 78, password 80, email address 82, name 84, and location 86, e.g., a zip code. Preferably, the gender, birthday, weight, and percent body fat designators are used to determine the customer's daily macronutrient allowances, as further described below.

For the percent body fat designator 70, the customer optionally enters their percent body fat, if known, or provides certain measurements and the customer's percent body fat is estimated based on methods known in the art. The goal designator is selected from one of the following dietary and health-related objectives: (1) "maximum fat loss," (2) "moderate fat loss," (3) "maintenance," (4) "build muscle," or (5) "athletic performance." Additionally, the meal planning system 10 can accommodate any number of other dietary/health-related goals, such as adjustments for diabetic customers and/or kosher dietary requirements. The first meal time designator 73 is used to designate the approximate time of the first meal and can be used along with the number of meals per day to set recommended times for each meal.

The customer also selects a meal program designator 74 to accommodate the customer's meal preparation skills, schedule, and access to ingredients. Preferably, the meal program designator balances meal preparation time with recipe variety and selection. For example, as shown in FIG. 6, the customer can select one of four meal program designators designated by titles as "Elite," "Comprehensive," "Basics Plus,"and "Basics." In one embodiment, if the customer selects meal program designator "Basics", the meal planning center generates recipes having an average preparation time of under five minutes and limits the corresponding recipes to select from approximately 50 ingredients. If the meal program designator "Basics Plus" is selected by the customer, the meal planning center includes recipes having preparation times up to 10 minutes, which choose from approximately 70 ingredients. Meal program designators "Comprehensive" and "Elite" further expand the selection to include recipes selected from ingredient lists of 120 and 230, respectively, with preparation times up to 15 and 20 minutes, respectively. It should be appreciated, however, that the meal program designator can be tailored to take additional or different considerations into account, such as cost, availability and inclusion of pre-manufactured food products.

The food preference designator 76 allows the customer to designate particular ingredients or entrees for inclusion or removal from the customer's meal plan, e.g., beef, chicken, dairy, lamb, pork, protein powder, seafood, tuna, or turkey. In various embodiments, the customer can select from an array of dietary considerations, such as, kosher or vegetarian diets. Also, the customer can optionally highlight particular entrees, categories of entrees, ingredients, or categories of ingredients as favorites, which will, in turn, increase their frequency in the customer's meal plan.

In one preferred embodiment, the customer selects an activity level designator 78 which best describes their current exercise regime. For example, the customer might select one of the following:

"None," currently do not exercise or engage in regular physical activity;

"Fat Loss Focus," walk or primarily participate in cardiovascular exercise for 20–30 minutes at least three times per week;

"Good Health," exercise somewhat intensely 30–40 minutes at least four times per week, primarily cardiovascular training but includes some resistance training;

"Strength Training," exercise intensely 45 minutes at least five times per week, primarily resistance training with some cardiovascular training;

"Muscle Building/Athletic Performance," exercise very intensely for at least 45 minutes six to seven times per week, primarily weight lifting with minimal cardiovascular training; or "Competitive Athlete," exercise very intensely for at least two hours six to seven times per week, training consists of heavy weight lifting and/or performance based endurance training.

Alternatively, the activity level designator can specifically denote the customer's activity level. For example, the customer can maintain a detailed record, manually or with the aid of a recording device, exercises performed along with a chronology of various measurements related to physical exertion and health such as heart rate, blood pressure, blood composition, oxygen intake, and so on, the compilation of which would be the customer's activity level designator.

The system requires the password 80, selected by the customer, to meet predetermined criteria, such as having at least 6 characters, and aids in protecting the customer's data. The email address 82, name designator 84, and the location designator 86 are used to identify the customer. The email address allows the system to communicate electronically with the client device.

Once the customer provides the information requested on the customer registration page, the "Submit" icon 88 is selected, thereby initiating steps S-3 and S-4 depicted in FIG. 4. The client device 12 transmits the customer's information to the meal planning center 14 via the Internet 16, where it is received by the web server 40 and, thereafter, stored in the customer account database 56 for use by the meal planning system.

Figure 7:
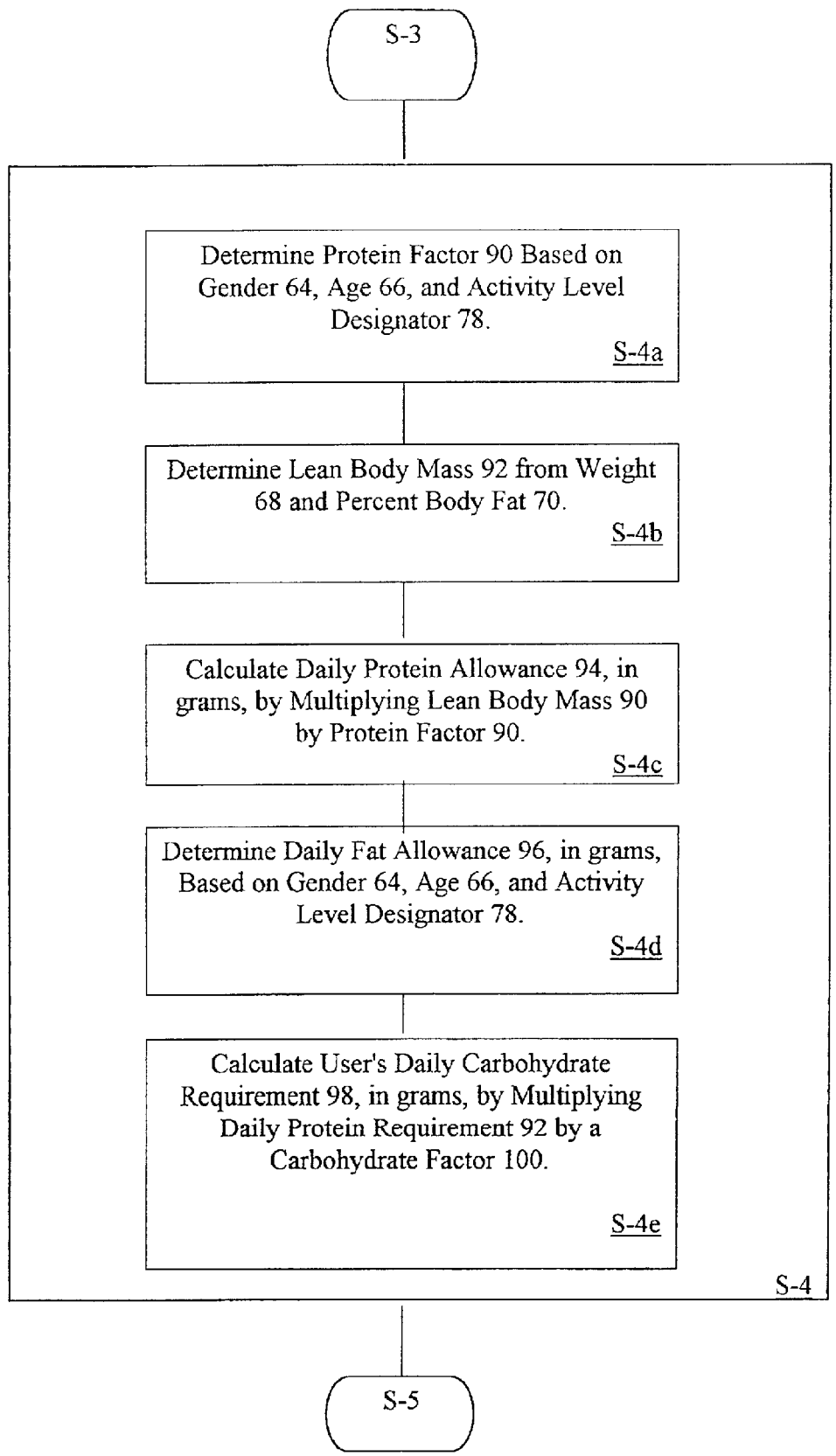
FIG. 7 is a flowchart depicting one preferred method of calculating nutrition factors.

At step S-4 depicted in FIG. 4, the meal planning center 14 calculates the customer's daily macronutrient allowances to achieve the customer's preselected goal, which is described in detail by steps S-4a to S-4e depicted in FIG. 7. Once step S-4 is initiated by the customer, the menu generating module 44 accesses the customer specific information in the customer account database 56. Preferably, daily consumption allowances of proteins, fats, and carbohydrates are calculated as outlined in FIG. 7; however, it can readily be seen that other embodiments can calculate varying combinations of these and other nutrients, such as fiber, vitamins, and minerals, using formulas or charts now known, or others which may be later derived.

Referring now to FIG. 7, at step S-4a, the menu generating module 44 determines a protein factor 90 based upon the customer's gender 64, age 66, and activity level designator 78. Sample protein factors are provided in Table A.

TABLE A

Protein Factor and Daily Fat Allowance

| Activity Level | Male Age 15–55 | | Female Age 15–50 | |
|---|---|---|---|---|
| | Protein Factor (g/lb) | Fat Rqmt (g) | Protein Factor (g/lb) | Fat Rqmt (g) |
| "None" | 0.6 | 40 | 0.8 | 35 |
| "Fat Loss Focus" | 0.7 | 45 | 0.9 | 40 |
| "Good Health" | 0.8 | 56 | 1.0 | 45 |
| "Strength Training" | 1.0 | 70 | 1.1 | 56 |
| "Muscle Building/Athletic Performance" | 1.1 | 110 | 1.2 | 70 |
| "Competitive Athlete" | 1.2 | 130 | 1.3 | 100 |

At step S-4b, the customer's lean body mass 92 is determined by subtracting the fat weight from the customer's total weight, fat weight is the percent body fat times total weight, e.g., "Customer A", a male weighing 200 pounds has 20 percent body fat, he would have a lean body mass of 160 pounds (weight−(weight×percent body fat)= lean body mass). As previously mentioned, the customer optionally enters their percent body fat, if known, or provides measurements and percent body fat is calculated based on approaches known in the art.

At step S-4c, the customer's daily protein allowance 94, in grams, is calculated by multiplying the customer's lean body mass by the protein factor 90, for example, if Customer A selected activity level "Fat Loss Focus," his protein factor would be 0.7 g./lb. and his daily protein allowance would be 112 grams (0.7×160 pounds). At step S-4d, the customer's daily fat allowance 96, in grams, is assigned based on customer's gender 64, age 66, and activity level designator 78 as shown in Table A, e.g., Customer A would be assigned 45 grams of fat, daily.

Then, at step S-4e, the customer's daily carbohydrate allowance 98, in grams, is determined by multiplying the daily protein allowance by a carbohydrate factor 100. The carbohydrate factor is assigned based upon the customer's goal designator 70, as shown in Table B below.

TABLE B

Carbohydrate Factor (g/lb)

| Goal | Male Age 15–55 | Female Age 15–50 |
|---|---|---|
| "Maximum Fat Loss" | 1.5 | 1.5 |
| "Moderate Fat Loss" | 1.7 | 1.7 |
| "Maintenance" | 2.0 | 2.0 |
| "Build Muscle" | 2.3 | 2.3 |
| "Athletic Performance" | 1.5 | 1.5 |

For example, if Customer A selected the "maximum fat loss" goal, he would be assigned a carbohydrate factor of 1.5 and, as a result, 168 grams of carbohydrates, daily (112 grams×1.5). Other embodiments of the invention include distributing the function of calculating customer specific nutritional values across more than one module, as well as, distributing the customer specific information across databases. It should be appreciated that the macronutrients need not be calculated in the aforementioned order to achieve the objectives of the invention. Also, meal planning center personnel such as a nutritionist can manually set customer specific nutritional values. Once step S-4 is completed by the menu generating module, without need for further prompting, the module will proceed to steps S-5 and S-6.

At step S-5 of FIG. 4, the menu generating module 44 selects recipe templates from the recipe template database 62 based on the customer's meal program designator 74 and food preference designator 76. In the recipe template database, the recipe templates are grouped according to meal-type (breakfast, snack, lunch, or dinner) and preparation time. The recipes are further assigned to subgroups, such as, breakfast-eggs, breakfast-oatmeal, snack-sandwiches, snack-nutrition bar, and so on. To provide variety and nutritional distribution, e.g., assigning seafood twice a week, the menu generating module, selects recipe templates from subgroups randomly and/or as scheduled by a meal planning center nutritionist. Once the daily nutritional allowances are determined, the menu generating module determines the number of meals per day and apportions fulfillment of the daily nutritional allowances amongst the meals. Preferably, the daily nutritional allowances are equally distributed. For example, as determined above, Customer A was allocated 112 grams of proteins, 168 grams of carbohydrates, and 45 grams of fat daily. Thus, he would be assigned 22 grams of protein, 34 grams of carbohydrates, and 9 grams of fat for each meal. In this embodiment, the meal planning system defaults to five meals per day, breakfast, lunch, dinner and two snacks, and will only vary if the daily protein allowance 94 divided by the number of meals, e.g., 5, is greater than or equal to 40 grams of protein per meal (P/5≧40) in which case additional snacks or meals will be added until the grams of protein per meal is less than 40 (P/N<40). Once, the number of meals and particular recipe templates are selected, the menu generating module will continue to step S-6.

Before describing step S-6, the ingredients database 58 and recipe template database 60 will be further described. FIGS. 8A and 8B depict ingredients database information transmitted from the data storage device 54 to the terminal 52. Nutritionists and/or system administrators at the meal planning center 14 can add, edit and delete ingredients and ingredient descriptions contained in the ingredient database using the ingredient input page, depicted in FIGS. 8A and 8B. Ingredients for inclusion to the database are selected based on factors such as nutritional contribution, glycemic index, taste, availability, versatility, and convenience. The system administrator inputs the ingredient's display names 102, unit measurement 104, and nutritional contribution factors 106. In the preferred embodiment, the nutritional contribution factors per unit measurement include, total grams, and contributions in grams of carbohydrates, protein, fat, fiber, sodium, and carbohydrates from sugar.

Figure 9:
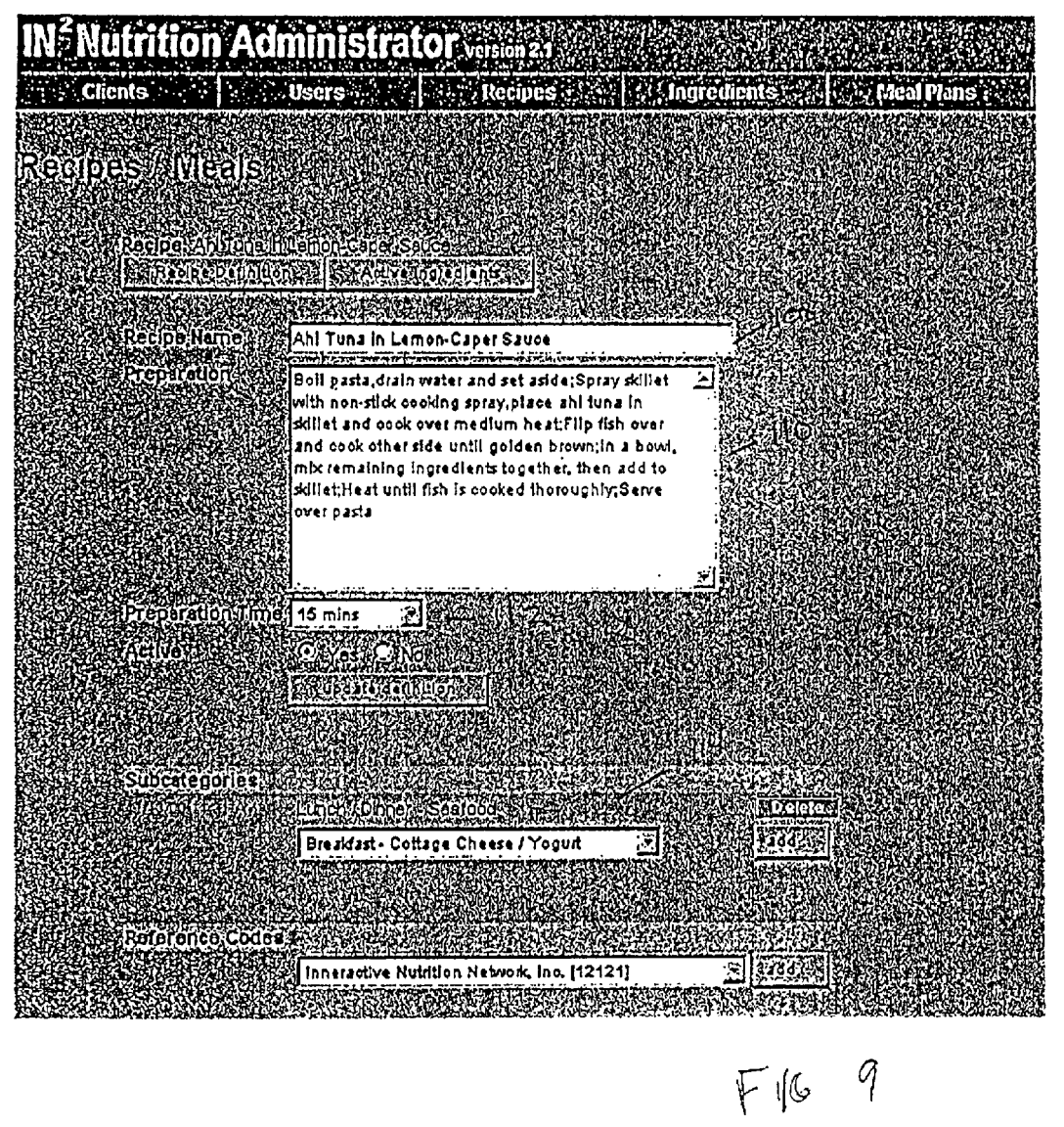

FIGS. 9 and 10 depict recipe template database information transmitted from the data storage device 56 to the terminal 54. In particular, FIGS. 9 and 10 depict a recipe template for "Ahi Tuna in Lemon-Caper Sauce." The recipe templates are configured to adjustably satisfy the macronutrient allowances determined at step S-4. Nutritionists and/or system administrators at the meal planning control center 14 can add, edit and delete recipe templates and recipe template information contained in the recipe template. In the preferred embodiment, each recipe template entry to the recipe template database 64 is assigned a name 108, preparation instructions 110, preparation time 112, a meal category 114, and ingredients. The ingredients assigned to a recipe template references the ingredient's data from the ingredients database 58. Within the recipe template, the associated ingredients are each further assigned "recipe rule factors", to include a nutritional function 116, an ingredient type 118, a priority value 120, a default value 122, a minimum ingredient value 124, and a maximum ingredient value 126. The meal category designator, preparation time, and listed ingredients are used by the menu generating module in the selection of particular recipe templates for the customer's meal plan as described above. The recipe rule factors are used by the menu generating module to create a recipe which satisfies the customer's macronutrient allowances, as well as, accounting for other considerations, such as taste and ease of preparation.

Referring back to FIG. 4, at step S-6, the menu generating module 46 uses the selected recipe templates to create recipes which satisfy the macronutrient allowances determined in step S-4. Using the recipe rule factors mentioned above, the menu generating module calculates the appropriate amount of each ingredient by adjusting selected ingredients from their default value 122. Specifically, the module uses the nutritional function 116 and priority value 120 to determine which ingredients to modify. For example in FIG. 10, pasta is assigned the nutritional function of "carbohydrate factor" with a priority value of one for that nutritional function. In building a recipe to satisfy the macronutrient allowance for carbohydrates of that meal, the menu generating module first determines whether the allowance is satisfied at the default values, if not, it increases the total grams of pasta from its default value until the carbohydrate allowance is satisfied, unless the maximum value for the ingredient is met or exceeded. Then, the menu generating module selects the ingredient assigned a priority value of two for the nutritional function, carbohydrate factor, to fulfill the carbohydrate allowance, and so on until the carbohydrate allowance for that meal is met. Preferably, the meal plan selectably includes recipes to satisfy a predetermined time period, e.g., 14 days, of nutritional allowances. Similar iterations are performed to fulfill the daily allowances for protein and fat. Preferably, the menu generating module performs iterations to sequentially satisfy the allowances for proteins then fats and then carbohydrates. Once, the iterations for each macronutrient allowance are performed for all meals of the meal plan, the menu generating module proceeds to step S-7. Other embodiments contemplate performing similar iterations to satisfy additional and/or different nutritional allowances, e.g., satisfying appropriate amount of nutrients such as sodium, fiber, and so on.

For ease of illustration, consider the following example of constructing a turkey sandwich recipe. In this example, "Customer B" has been allotted 30 grams of protein, 12 grams of fat, and 48 grams of carbohydrates and the menu generating module 44 has selected a turkey sandwich recipe template having the ingredients and recipe rule factors detailed in Table C.

TABLE C

Turkey Sandwich Recipe Template

| Ingredients (nutritional contribution/unit) | Function | Priority | Default Units | Min | Max |
| --- | --- | --- | --- | --- | --- |
| Bread (12 g of carbohydrates, 4 g of protein/slice) | — | — | 2 | 2 | 2 |
| Lettuce (1 g of carbohydrates/cup) | C | 2 | 0 | 0 | 2 |
| Tomato (5 g of carbohydrates/½ med. tomato) | C | 1 | 1 | 1 | 2 |
| Turkey Breast (5 g of protein/slice) | P | 1 | 2 | 2 | 7 |
| Mustard (1 tsp.) | — | — | 2 | 2 | 2 |
| Oil (3.5 g of fat/½ med. tsp.) | F | 1 | 3 | 3 | 10 |
| Apple (10 g of carbohydrates/½ med. apple) | C | 3 | 0 | 0 | 2 |

Using the default units, the turkey sandwich recipe template would result in a recipe having 18 grams of protein, 7.5 grams of fat, and 29 grams of carbohydrates, which does not satisfy Customer B's macronutrient allowances. Thus, the menu generating module would determine the appropriate measures of the ingredients to satisfy the macronutrient allowances for this meal.

First, the menu generating module will endeavor to satisfy Customer B's protein allowance of 30 grams within ±3 grams. The menu generating module will select the ingredient assigned the function of protein with the priority of one, which in this example is turkey breast. Then, the menu generating module will adjust the allocation of turkey breast to the recipe an amount, up to the maximum (seven slices) to reach Customer B's protein allowance. In this example, the system would assign four slices of turkey breast to the recipe, totaling 28 grams of protein.

Next, the menu generating module will endeavor to satisfy Customer B's fat allowance of 11 grams within ±3 grams. Here, the menu generating module will adjust the ingredient assigned priority one for fat, oil, from the default of 3 units (1.5 tsp.) to by adding an additional unit of oil, totaling 2 tsp. The resulting total fat content is 11 grams, which is within ±3 grams of Customer B's fat allowance.

The menu generating module 44 would then, adjust the recipe template to satisfy the carbohydrate allowance of 48 grams within ±6 grams. Here the sum of default units provides for a recipe with 29 grams of carbohydrates. The menu generating module would first adjust the ingredient assigned the function of carbohydrate with the priority of one, which in this example is tomato, up to its maximum of two units of satisfy the carbohydrate allowance, equaling 34 grams of carbohydrates for the recipe. Not being within ±6 grams of 48 grams, the menu generating module would next adjust the ingredient assigned the function of carbohydrate with the priority of two, lettuce. Set at its maximum amount of two cups, lettuce contributes an additional two grams of carbohydrates, totaling 36 grams. Being the ingredient assigned the function of carbohydrate with the priority of three, apple's amount would be adjusted from its default to reach Customer B's carbohydrate allowance. The menu generating module would add one half of an apple to the meal, thereby contributing nine grams of carbohydrates for a total of 45 grams. Thus, the recipe for Customer B's turkey sandwich includes the ingredients and amounts shown in Table D which provides 28 grams of protein, 11 grams of fat, and 45 grams of carbohydrates.

TABLE D

Turkey Sandwich Recipe Template

| Ingredient | Measurement |
| --- | --- |
| Bread | 2 slices |
| Lettuce | 1 cup |
| Tomato | 1 medium sized |
| Turkey Breast | 4 slices |
| Mustard | 2 tsp |
| Oil | 2 tsp |
| Apple | ½ medium sized |

At step S-7, the meal planning center 14 provides the customer with a personalized meal plan for a selected number of days, typically a seven day plan will be provided. FIG. 11 is a sample meal plan page transmitted by meal planning center and received by the client device 12. The customer selects a recipe name to view the recipe instructions. Also, the customer can print all recipes instructions by clicking on the "Print all meals" icon. By selecting a "Shopping list" icon 128, the customer proceeds to steps S-8 and S-9.

At step S-8, the menu generating module generates a shopping list of all ingredients within the customer's customized meal plan, and at step S-9 the meal planning system transmits the shopping list to the client device 12. FIG. 12 is a sample shopping list. Using the location designator 86 the meal planning system can recommend local stores which carry the products on the customer's shopping list. Additionally, the meal planning system can also provide locations for providers of prepared meals, such as, restaurants which provide meals that satisfy the customer's customized meal plan.

At step S-10, the meal planning system periodically requests updated customer information allowing the customer to update any of the information provided as step S-2. Such requests can be sent by e-mail. Step S-10 can also be initiated by the client without prompting from the meal planning system. FIG. 13 depicts a customer update page accessed by the customer with the client device 12. For example, the customer can provide updated information for the weight designator 72 and percent body fat designator 70.

At step S-11, the meal planning system will use the updated customer information to assess whether the selected goal 72 has been achieved. If the goal has not been achieved, the meal planning system reiterate the process starting at step S-3 with the updated customer information.

It should be appreciated from the foregoing description that the present invention provides a meal planning system and associated method for providing personalized meal plans optimized to achieve a selectable health objective which requires minimal research, effort, time, computation and record keeping. This is achieved, in part, by providing personalized meal planning which includes a client device and a meal planning center configured to communicate with the client device, and to receive a customer's information including a weight designator, a gender designator, a goal designator, and an activity level designator. The meal planning center includes a storage device and a processing unit. The storage device is configured to store recipe template files having an ingredient designator and a plurality of recipe rule factors, which include a nutrient contribution value, a minimum ingredient value, and a maximum ingredient value. A plurality of recipe rule factors are each assigned to each ingredient designator. The processing unit is configured to determine a nutritional allowance based upon the customer information and to create a recipe that satisfies the nutritional allowance by using the recipe rule factors assigned to the ingredient. The meal planning center is further configured to transmit the recipe to the client device.

The foregoing detailed description of the present invention is provided for the purposes of illustration and is not intended to be exhaustive or to limit the invention to the precise embodiment disclosed. Accordingly, the scope of the present invention is defined by the following claims.

I claim:

1. In a computerized meal planning system having a communications device, a data storage device, and a processing unit in communication with both the data storage device and the communications device, a method of meal planning comprising:

receiving client information via electronic transmission to the communications device, the client information including designators denoting weight, gender, goal, activity level, and lean body mass;

executing computer-readable instructions by the processing unit for assigning a plurality of nutritional allowances, including nutritional allowances for carbohydrates, proteins, and fats, the plurality of nutritional allowance based on the client information;

executing computer-readable instructions by the processing unit for selecting a recipe template from a database on the data storage device, the recipe template having, a plurality of ingredient designators, and
a plurality of recipe rule factors assigned to each ingredient designator to include,
at least one contribution value per unit measurement of ingredient for at least one of the plurality of nutrients,
a minimum allocatable amount of ingredient,
a maximum allocatable amount of ingredient, and
a nutritional priority value assigned to each ingredient designator annotating priority of use in satisfying one of the plurality of nutritional allowances;

executing computer-readable instructions by the processing limit for setting a recipe allocation amount for each ingredient within a range bounded by the minimum allocatable amount and a maximum allocatable amount for each ingredient to satisfy the plurality of nutritional allowances within a predetermined range for each nutritional allowance, the computer-readable instructions further including instructions that sequentially determine amounts for each ingredient based upon the nutritional priority values, wherein the nutritional priority value assigned to each ingredient denotes priority along an ordinal range having a first priority and subsequent priorities through to a lowest priority for at least one of carbohydrates, proteins, and fats, thereby resulting in a recipe having nutritional contributions of carbohydrates, proteins, and fats within the predetermined range for each of the plurality nutritional allowances; and delivering a recipe with each ingredient and corresponding recipe allocation amount to the client device via electronic transmission.

2. A method of meal planning as defined in claim 1; the computer-readable instructions that set a recipe allocation amount for each ingredient designator further comprising:

(a) instructions for determining if the nutritional allowance of a selected nutrient from the plurality of nutrients is satisfied with the plurality of ingredients set at default values and proceeding to following steps if no;

(b) instructions for selecting an ingredient assigned the highest priority value for the selected nutrient;

(c) instructions for attempting to satisfy the nutritional allowance of the first nutrient by adjusting the recipe allocation amount of selected ingredient from the minimum allocatable amount up to the maximum allocatable amount, proceeding to step (d) if not satisfied and if satisfied skipping to step (f);

(d) inscriptions for selecting a subsequent ingredient assigned a subsequent priority along the ordinal range for the first nutrient;

(e) instructions for attempting to satisfy the nutritional allowance of the selected nutrient by adjusting the recipe allocation amount of the subsequent ingredient from the minimum allocatable amount up to the maximum allocatable amount, repeating step (d) if not satisfied and if proceeding following steps; and (f) instructions for repeating steps (a) through (e) for all of the plurality of nutrients.

3. A meal planning system for automated meal planning comprising:

a communications device configured to receive client information from a client device, the client information including designators denoting weight, gender, goal, activity level, and lean body mass;

data storage device configured to store recipe template flies having, a plurality of ingredient designators, and a plurality of recipe rule factors assigned to each ingredient designator to include at least one contribution value per unit measurement of ingredient for at least one of the plurality of nutrients, a minimum allocatable amount of ingredient, a maximum allocatable amount of ingredient, a nutritional priority value assigned to each ingredient designator annotating priority of use in satisfying one of the plurality of nutritional allowances, the nutritional priority value assigned to each ingredient denotes priority along an ordinal range having a first priority and subsequent priorities through to a lowest priority for at least one of the plurality of nutrients;

a computer-readable medium having computer-readable instructions stored therein, the instructions including, instructions for creating a recipe having prescribed nutritional contributions of carbohydrates; proteins, and fats, wherein the prescribed nutritional contributions are based upon a client's nutritional allowances for carbohydrates, proteins, and fats, the recipe being created from the recipe template retrieved from the database on the data storage device, and instructions for setting a recipe allocation amount for each ingredient within a range bounded by the minimum allocatable amount and a maximum allocatable amount for each ingredient, thereby resulting in the recipe having the prescribed nutritional contributions of carbohydrates, proteins, and fats; and at least one processing unit in communication with the data storage device, the computer-readable medium, and the communications device via electronic transmission, the at least one processing unit configured execute the instructions on the computer-readable medium, thereby generating the recipe.

4. A meal planning system as defined in claim 3, wherein the communications device is further configured to transmit the recipe to the client device.

5. A meal planning system as defined in claim 3, wherein the at least one processing unit comprises a plurality of processing units.

6. A meal planning system as defined in claim 5, wherein each processor of the plurality of processing units is in communication with the data storage device, the computer-readable medium and the communications device, and is configured execute the instructions on the computer-readable medium.

7. A meal planning system as defined in claim 5, wherein the plurality of processing units in the aggregate is in communication with the data storage device, the computer-readable medium, and the communications device, and is configured-execute the instructions on the computer-readable medium.

8. In a computerized meal planning system having a communications device, a data storage device, and a processing unit in communication with both the data storage device, a method of meal planning comprising:

executing computer-readable instructions by the process unit that create a recipe having prescribed nutritional contributions of carbohydrates, proteins, and fats, wherein the prescribed nutritional contributions are based upon a client's nutritional allowances for carbohydrates, proteins, and fats, the recipe being created from a recipe template retrieved from a database on the data storage device, the recipe template having, a plurality of ingredient designators, and recipe rule factors assigned to at least three ingredient designators, the rule factors of each ingredient designator including, a contribution value per unit measurement of ingredient selected from a list consisting of carbohydrates per unit measurement, proteins per unit measurement, and fats per unit measurement, a minimum allocatable amount of ingredient, a maximum allocatable amount of ingredient, and a nutritional priority value assigned to each ingredient designator annotating priority of use in satisfying one of the plurality of nutritional allowances, the nutritional priority value assigned to each ingredient denoting priority from a first priority through to a lowest priority for at least one of the plurality of nutrients;

the instructions including instructions that set a recipe allocation amount for each ingredient within a range bounded by the minimum allocatable amount and a maximum allocatable amount for each ingredient, thereby resulting in the recipe having the prescribed nutritional contributions of carbohydrates, proteins, and fats; and delivering the recipe to a client device via electronic transmission.

9. A method of meal planning as defined in claim 8, the instructions that set a recipe allocation amount for each ingredient further comprising:

(a) instructions for determining if the nutritional allowance of a selected nutrient from the plurality of nutrients is satisfied with the plurality of ingredients set at default values and proceeding to following steps if no;

(b) instructions for selecting an ingredient assigned the highest priority value for the selected nutrient;

(c) instructions for attempting to satisfy the nutritional allowance of the first nutrient by adjusting the recipe allocation amount of selected ingredient from the minimum allocatable amount up to the maximum allocatable amount, proceeding to step (d) if not satisfied and if satisfied skipping to step (f);

(d) instructions for selecting a subsequent ingredient assigned a subsequent priority along the ordinal range for the first nutrient;

(e) instructions for attempting to satisfy the nutritional allowance of the selected nutrient by adjusting the recipe allocation amount of the subsequent ingredient from the minimum allocatable amount up to the maximum allocatable amount, repeating step (d) if not satisfied and if proceeding following steps; and (f) instructions for repeating steps (a) through (e) for all of the plurality of nutrients.

* * * * *

UNITED STATES PATENT AND TRADEMARK OFFICE
CERTIFICATE OF CORRECTION

PATENT NO. : 6,872,077 B2
DATED : March 29, 2005
INVENTOR(S) : John J. Yeager

It is certified that error appears in the above-identified patent and that said Letters Patent is hereby corrected as shown below:

Column 13,
Line 8, please change "flies" to -- files --
Line 11, please change "inseriptions" to -- instructions --
Line 21, please change "denotes" to -- denoting --

Signed and Sealed this

Twenty-eighth Day of June, 2005

JON W. DUDAS
*Director of the United States Patent and Trademark Office*